US00PP22258P2

(12) United States Plant Patent
Adam, Jr.

(10) Patent No.: US PP22,258 P2
(45) Date of Patent: Nov. 15, 2011

(54) ***TIARELLA* PLANT NAMED 'STEPHANIE COHEN'**

(50) Latin Name: *Tiarella cordifolia*
Varietal Denomination: Stephanie Cohen

(75) Inventor: Sinclair A. Adam, Jr., Coatesville, PA (US)

(73) Assignee: Plants Nouveau-a division of Treadwell Palmer International Inc., Baltimore, MD (US)

( * ) Notice: Subject to any disclaimer, the term of this patent is extended or adjusted under 35 U.S.C. 154(b) by 0 days.

(21) Appl. No.: 12/806,647

(22) Filed: Aug. 18, 2010

(51) Int. Cl.
*A01H 5/00* (2006.01)

(52) U.S. Cl. ..... Plt./486

(58) Field of Classification Search ..... Plt./486
See application file for complete search history.

*Primary Examiner* — Annette Para
(74) *Attorney, Agent, or Firm* — Penny J. Aguirre

(57) ABSTRACT

A new cultivar of *Tiarella cordifolia*, 'Stephanie Cohen', characterized by its compact mounding clump growth habit, its white flowers on single and branched flower racemes that emerge from pink flower buds, its unique foliage coloration with ovate, glossy, rugose, deeply lobed leaves with maroon center markings, in fall the leaves turn darker green and in winter the foliage is purple-red and remains glossy, and its ability to form dense stands particularly suited for garden border planting, ornamental ground cover, shaded areas, and ecology and restoration planting.

2 Drawing Sheets

Botanical classification: *Tiarella cordifolia.*
Cultivar designation: 'Stephanie Cohen'.

CROSS REFERENCE TO A RELATED APPLICATION

This application is co-pending with a U.S. Plant Patent Application filed for a plant derived the Inventor's breeding program that is entitled *Tiarella* Plant Named 'FM Mooberry' (U.S. Plant patent application Ser. No. 12/806,640).

BACKGROUND OF THE INVENTION

The present invention relates to a new and distinct cultivar of *Tiarella* plant, botanically known as *Tiarella cordifolia* 'Stephanie Cohen' and will be referred to hereafter by its cultivar name, 'Stephanie Cohen'.

The Inventor discovered the new cultivar, 'Stephanie Cohen', in a trial plot at his nursery in Coatesville, Pa., in 2007. The parentage of the new variety is the result of open-pollinated plants of *Tiarella cordifolia*, and *Tiarella cordifolia* var. *collina*. The exact parentage is unknown as several hundred cultivars and unnamed plants from the Inventors breeding program were grown for seed production. The new cultivar, 'Stephanie Cohen', was selected for its unique growth habit, flower stem branching, and distinctive foliage coloration throughout the growing season.

Asexual reproduction of the new cultivar was first accomplished by division in Coatesville, Pa. by the Inventor in 2007. Propagation by division and subsequently by tissue culture has determined that the characteristics of this cultivar are stable and are reproduced true to type in successive generations.

SUMMARY OF THE INVENTION

The following traits have been repeatedly observed and represent the characteristics of 'Stephanie Cohen'. These attributes in combination distinguish 'Stephanie Cohen' as a new and distinct cultivar of *Tiarella.*

1. 'Stephanie Cohen' exhibits a compact mounding clump growth habit.
2. 'Stephanie Cohen' exhibits white flowers on single and branched flower racemes that emerge from pink flower buds.
3. 'Stephanie Cohen' exhibits unique foliage coloration with ovate, glossy, rugose, deeply lobed leaves with maroon center markings, in fall the leaves turn darker green and in winter the foliage is purple-red and remains glossy.
4. 'Stephanie Cohen' forms form dense stands particularly suited for garden border planting, ornamental ground cover, shaded areas, and ecology and restoration planting.

'Stephanie Cohen' can be most closely compared to 'FM Mooberry', which is similar in having a clump-forming plant habit. 'FM Mooberry' differs most significantly from 'Stephanie Cohen' in having leaves that are less deeply lobed with larger maroon marking and in having less glossy foliage. In addition, the white flowers of 'FM Mooberry' emerge from white flower buds rather than pink. 'Stephanie Cohen' can also be compared the cultivar 'Brandywine' (not patented), which is similar in having a clump-forming plant habit. 'Stephanie Cohen' differs from 'Brandywine' in foliage that is more finely dissected and much glossier and in having flower buds that are pink in color rather than white.

BRIEF DESCRIPTION OF THE DRAWING

The accompanying colored photographs illustrate the overall appearance and distinct characteristics of the new *Tiarella*. The photographs were taken of two year-old plants of 'Stephanie Cohen' as grown outdoors in one-gallon containers in Coatesville, Pa.

The photograph in FIG. 1 was taken in April and illustrates the spring foliage and flower buds.

Figure 1:
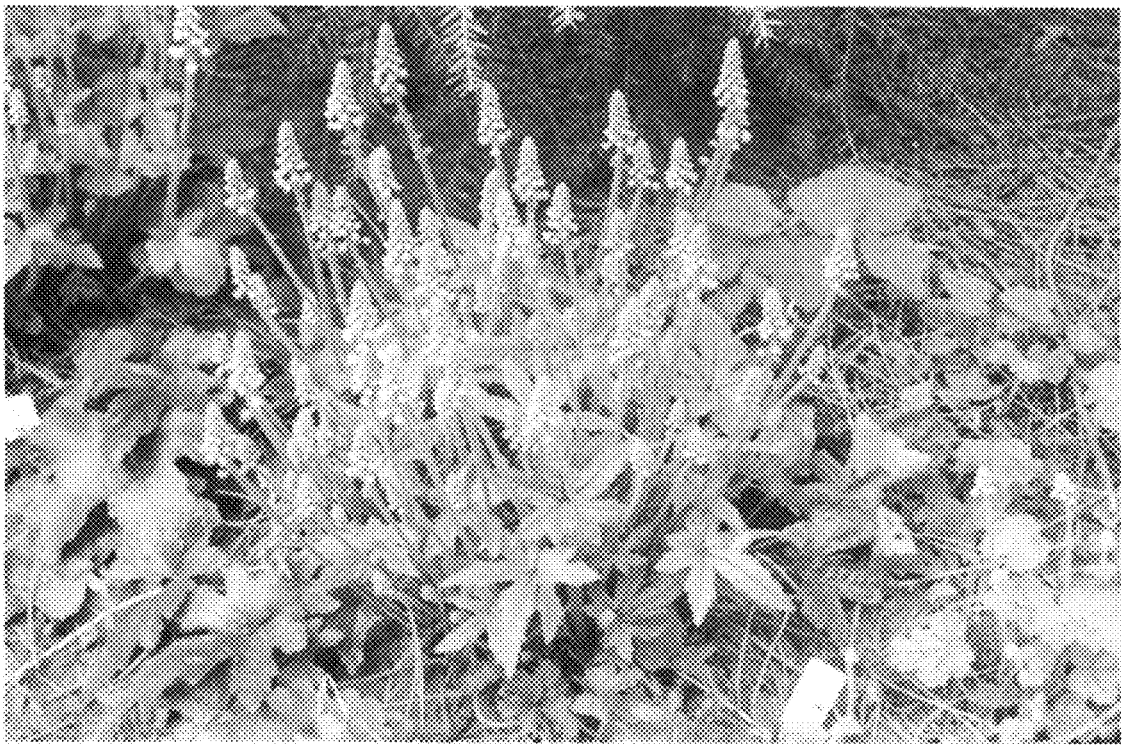
Figure 2:
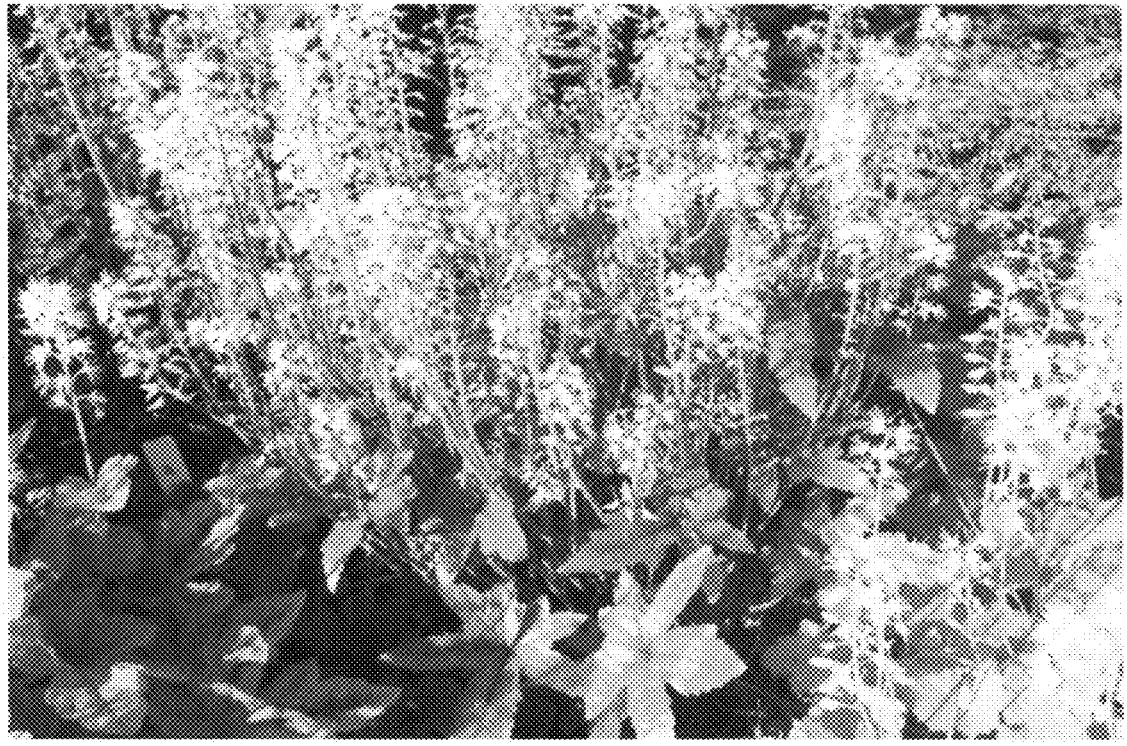

The photograph in FIG. 2 was taken in May and provides a close-up view of the mature foliage and blooms of 'Stephanie Cohen'. The colors in the photographs are as close as possible with the digital photography and printing techniques utilized and the color codes in the detailed botanical description more accurately describe the colors of the new *Tiarella*.

DETAILED BOTANICAL DESCRIPTION OF THE PLANT

The following is a detailed description of two-year-old plants grown outdoors and in the greenhouse in one-gallon containers during 2007 and 2008 at Coatesville, Pa., USA. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Botanical classification: 'Stephanie Cohen' is a cultivar of *Tiarella cordifolia*.

General characteristics:

*Plant habit.*—Compact mounding clump.

*Blooming.*—Abundant in May, and sporadically thereafter during the summer and fall.

*Plant height.*—Approximately 17 to 22 cm without blooms, and approximately 28 to 32 cm with blooms.

*Plant width.*—Approximately 20 to 24 cm (1 year plant), 38 to 42 cm (2 year plant).

*Diseases and pests.*—No susceptibility to diseases has been noted during observations to date.

*Root description.*—Fibrous roots.

*Hardiness.*—U.S.D.A. Zones 4 to 7.

*Branching habit.*—Basal rosette.

*Propagation.*—Division and flower stem cuttings.

*Vigor.*—Moderate.

Foliage description:

*Leaf shape.*—Palmately lobed, 5 to 7 lobed, the central one being more pronounced developing shoulder lobes 3 to 4 cm behind leaf tip at maturity, lobes broadly obtuse to rounded and cuspidate.

*Leaf division.*—Simple.

*Leaf margins.*—Crenate at leaf maturity, doubly serrate in juvenility.

*Leaf size.*—Approximately 9 to 12 cm in length, 8 to 10 cm in width.

*Leaf apex.*—Acute.

*Leaf base.*—Cordate.

*Leaf surface.*—Rugose, upper surface; glossy and setulose with setae 2 mm in length and NN155C in color, lower surface; matte, glabrous.

*Leaf arrangement.*—Basal clump.

*Leaf venation.*—Palmately reticulate, upper surface; fine, slightly translucent, 144C in color, lower surface; prominently raised, pubescent, a blend of 148C and 144C.

*Leaf color.*—Summer emerging upper surface; 144A to 144B and 187A at center and along main vein, summer emerging lower surface; 146B to 146C, summer mature upper surface; N137B to 137C and 200B at center and along main vein, summer mature lower surface; 146B to 191A, fall mature upper and lower surface containing patches with midtones near 53D and darker patches 187A and 187B, winter color upper and lower surface about N77C in color.

*Leaf attachment.*—Petiolate.

*Petiole.*—Approximately 12 to 14 cm in length, 2 mm in diameter, surface pubescent, color 145C, a blend of 178B and 177B towards base.

Inflorescence description:

*Inflorescence type.*—Raceme and perfect (bisexual).

*Bearing.*—On a branched stalk commonly having a height of approximately 28 to 34 cm, with a cauline leaf. Subsequently, branched racemes emerge; 2 to 8 cm in length.

*Inflorescence size.*—About 15 cm in length (from base of raceme) and 4 cm in width.

*Number of blooms per raceme.*—Approximately 50 to 60 blooms and main racemes and 10-20 blooms on branches.

*Flower buds.*—Globose in shape, about 3 mm in length and 2 mm in width, 75C to 75D in color.

*Flower size.*—Approximately 8 to 10 mm on average per floret.

*Flower fragrance.*—Slight and sweet.

*Lastingness of flowers.*—About 4 days.

*Calyx.*—Five-lobed, sepals fused at base, 145D in color.

*Petals.*—Five, triangular in shape, surface glabrous, color upper and lower surface NN155C.

*Pedicel.*—Approximately 7 to 10 mm in length on average and 1.5 mm in width, surface pubescent, color 195C.

*Androecium.*—10 stamens, anthers 30A in color, pollen not observed.

*Gynoecium.*—1 pistil.

*Fruit/seeds.*—Approximately 1400 to 1600 seeds, 0.3 grams per plant.

It is claimed:

1. A new and distinct cultivar of *Tiarella* plant named 'Stephanie Cohen' as herein illustrated and described.

* * * * *